United States Patent [19]

Conway et al.

[11] 4,102,344
[45] Jul. 25, 1978

[54] STIMULATOR APPARATUS FOR INTERNAL BODY ORGAN

[75] Inventors: Christopher J. Conway, Edina; Eugene G. Glover, St. Paul, both of Minn.

[73] Assignee: Mentor Corporation, Minneapolis, Minn.

[21] Appl. No.: 741,948

[22] Filed: Nov. 15, 1976

[51] Int. Cl.² .............................................. A61N 1/32
[52] U.S. Cl. ............................ 128/419 E; 128/423 R
[58] Field of Search ........ 128/419 C, 419 E, 419 PG, 128/419 PS, 419 R, 421, 422, 423

[56] References Cited

U.S. PATENT DOCUMENTS

| | | | |
|---|---|---|---|
| 3,357,434 | 12/1967 | Abell | 128/419 E |
| 3,662,758 | 5/1972 | Glover | 128/419 E |
| 3,667,477 | 6/1972 | Susset et al. | 128/419 E |
| 3,796,221 | 3/1974 | Hagfors | 128/419 C |

OTHER PUBLICATIONS

Richwien et al., "Medical and Biological Engineering", vol. 4, No. 2, Mar. 1966, pp. 193-195.
Goovaerts et al., "Medical Research Engineering", vol. 10, No. 4, Sep. 1971, pp. 28-30.
Davies, "Journal of the British Institute of Radio Engineers", vol. 24, No. 6, Dec. 1962, pp. 453-456.

*Primary Examiner*—William E. Kamm
*Attorney, Agent, or Firm*—Frederick E. Lange

[57] ABSTRACT

An implantable unit for stimulating an internal body organ in which there is a power supply portion for having power induced therein from a source external of the body and electrodes adapted to be attached to a muscular organ such as a bladder or the like, said unit having an energy storage device, such as a capacitor, connected to the electrodes under the control of a transistor which is normally maintained non-conductive as a result of the voltage drop across an impedance connected to the power supply so that each time that the power supply is interrupted, the transistor becomes conductive to discharge the energy storage device through the electrodes and apply a stimulating voltage to the organ. The transmitter source external of the body is designed to periodically interrupt for a short period the voltage transmitted thereby so that the voltage produced by the power supply of the implantable unit is thus periodically interrupted. The sole means for holding the transistor of the implantable unit non-conductive is the impedance connected across the power supply so that as soon as the voltage from the power supply disappears, the transistor becomes conductive. The implantable unit has no internal power supply and its sole source of power is that derived from the transmitter.

10 Claims, 7 Drawing Figures

STIMULATOR APPARATUS FOR INTERNAL BODY ORGAN

BACKGROUND OF THE INVENTION

It has become common practice to provide implantable stimulating devices for stimulating the operation of a muscular organ, the operation of which has become impaired through injury to other portions of the body without injury to the organ itself. One example of this is the urinary bladder which is controlled by the brain through the spinal cord and a peripheral system of nerves connected between the spinal cord and the bladder. A disturbance to one of these nerves or nerve systems will often result in impairment of the ability of the patient to empty his bladder properly even though the muscle tissue of the bladder itself is healthy.

One method which has been employed very successfully in overcoming this problem is that of an implantable stimulator which is effective to stimulate the organ in question at desired times. Such a stimulator normally employs electrodes which are attached to the muscular organ at suitable points adjacent normal nerve connections and is effective to apply to such electrodes stimulus pulses at a frequency such that the organ is caused to operate in the desired manner. In the case of a urinary bladder, the stimulator is actuated at a time when it is desired to void the bladder.

While certain of such implantable units have a battery associated therewith, it is desirable where the implantable unit is to be operated only at preselected times to have the battery in an external transmitting unit so that the implantable unit employs purely passive components and receives all of its energy from the transmitting unit. In this way, it is possible to have an implantable unit which has an unlimited life.

Basically, there are two types of implantable units which receive their energy from an external source. One of these is the type which delivers the received energy directly, as with a tuned tank circuit, and transmits it in the form received to the electrodes. The other type is the type which has an energy storage element that is charged and periodically discharged to apply voltage pulses to the electrodes at the desired intervals.

The problem that has existed in connection with the latter type of unit is that the mechanism for controlling the discharge of the energy storage element has been relatively complicated. In one particular case, this has taken the form of a shift register which is advanced in accordance with pulses from the transmitting unit and which has variable outputs to selectively and periodically trigger electronic switches causing the energy storage devices associated with respective electrodes to discharge and apply a voltage to the associated electrodes.

SUMMARY OF THE INVENTION

The present invention is concerned with apparatus for periodically stimulating an internal body organ under the selective control of a transmitter located outside the body in which there is an implantable unit having an energy storage device connected to an electrode under the control of an electronic switching device with a voltage obtained from the transmitter, by means such as an impedance means, maintaining the switching device nonconductive only while the receiver of the implantable unit is receiving an output from the transmitter so that each time that said output ceases, the switching device becomes conductive to cause the energy storage device to energize the electrode to stimulate the organ. This is accomplished automatically as a result of the transmitted voltage from the transmitter ceasing and not by reason of the interposition of some active device actuated in response to pulses received from the transmitting unit. Specifically, the implantable unit has a power supply portion having means reactively coupled with the transmitter unit for producing a voltage during each duration of the high frequency output of the transmitter unit.

The energy storage device is preferably a capacitor which is charged while the electronic switching device is nonconductive and is discharged each time that the switching device becomes conductive.

The electronic switching device may take the form of a transistor having a collector and emitter in series with the energy storage device and with the electrodes, and a base which is so connected to the impedance means that the potential of the base relative to the emitter is such that during the existence of the signal from the transmitter no substantial current flow will take place in the emitter-collector circuit. Specifically, the impedance means may be a resistor connected across the output terminals of the power supply portion.

The power supply of the implantable unit may be a coil inductively connected with a transmitting coil in the transmitting unit and which includes a rectifier for rectifying the induced current and a filter for minimizing the pulsations in the output of the power supply unit. This rectifier is preferably a full wave rectifier. Preferably, some constant voltage drop means is employed in the output of the power supply unit to limit the voltage supplied by the power supply.

Other features and objects of the invention will be apparent from a consideration of the accompanying specification claims and drawing.

BRIEF DESCRIPTION OF THE DRAWING

Referring to FIG. 1, the housing of the implantable unit is generally indicated by the reference numeral 10. This housing encloses the various circuitry to be described. This circuitry may be encapsulated in epoxy resin which in turn is coated with an implantable grade of silicone rubber. As will be noted from FIG. 1, the housing 10 is relatively smooth and adapted for reception by a suitable pocket in the body formed by a section between muscular layers. Secured to the housing 10 are four electrode leads 11, 12, 13 and 14. Electrode leads 11 and 12 form one bipolar electrode 17 and leads 13 and 14 a second bipolar electrode 18. The leads 11 and 12 are protected through all but a terminal portion of their length by an insulating sheath 19, which may be of flexible silicone rubber and are sealed together at their outer ends by a suitable seal 15. Similarly, leads 13 and 14 are protected by a sheath 20 of the same material and are sealed together at their outer ends by a seal 16. The leads 11, 12, 13 and 14 are preferably formed of some metal such as platinum which may be woven with strands of surgical suture material to hold the leads in spaced relation. A typical type of arrangement of this type is shown in the Timm et al U.S. Pat. No. 3,760,812. The particular construction of these electrodes, however, forms no part of the present invention. In use, the electrodes 11, 12 and 13, 14 are secured adjacent the bladder so that upon a voltage existing between the leads of either pair, a current flows through the bladder tissue.

FIG. 2 shows an exterior view of the transmitter unit. It will be noted that this is provided with a housing 20 having a switch 21 projecting from the side thereof. The switch 21 is a push button switch which is pressed whenever it is desired that a signal be transmitted to the receiver. While the nature of the transmitter is important as far as the present invention is concerned, the novelty resides in the receiver itself and the manner in which it cooperates with the transmitter. As shown in FIG. 3, the transmitter basically comprises a transmitter oscillator 22 which may produce a frequency of approximately 300 kilohertz. It may have a power output of approximately 20 watts. The oscillator is connected to an induction or transmitting coil 23. A trigger generator 24 is employed to periodically interrupt the output of the transmitter oscillator. For example, the 300 kilohertz output of the oscillator 22 may be interrupted by the trigger generator 24 for 1½ milliseconds every 50 milliseconds.

The transmitter coil 23 thus transmits a signal of 300 kilohertz. This transmission is interrupted every 50 milliseconds for 1½ milliseconds. As will be pointed out, it is these interruptions of the transmission which causes a voltage pulse to be applied to the electrodes 17 and 18.

A transmitter of the general type discussed is described in the Glover U.S. Pat. No. 3,662,758. While the transmitter there performed additional functions not necessary in the present device, the basic operation is very similar.

Figure 1:
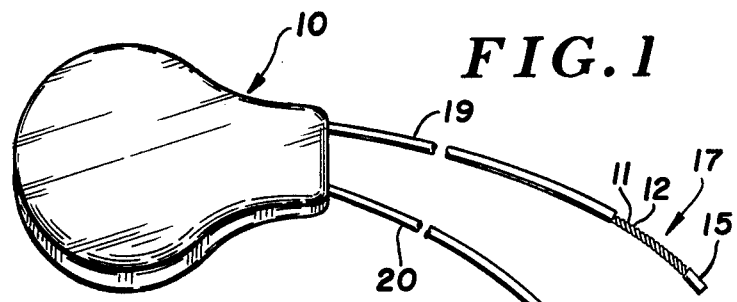
FIG. 1 is a perspective view of the implantable unit of the present invention.
Figure 2:
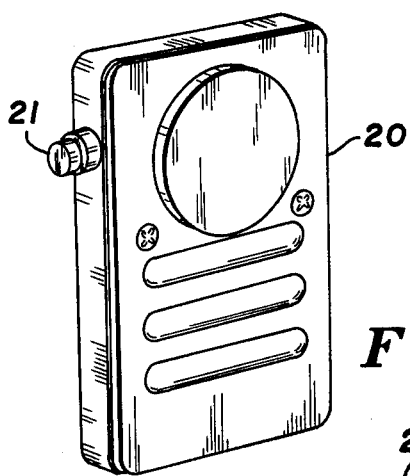
FIG. 2 is a perspective view of the transmitter unit.
Figure 3:
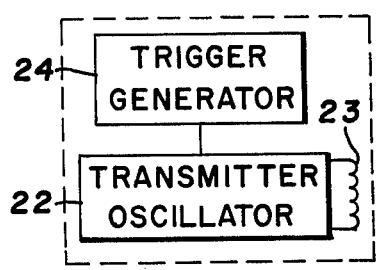
FIG. 3 is a schematic view in block diagram form of the transmitter unit.
Figure 4:
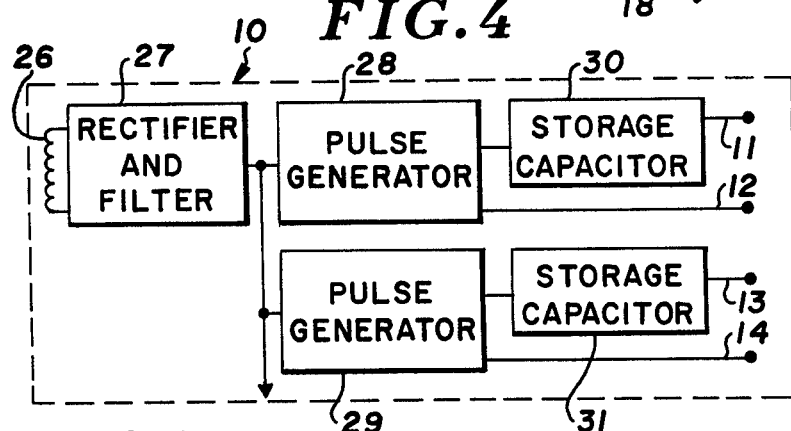
FIG. 4 is a schematic view in block diagram form of the implantable unit.

Referring now to FIG. 4 which shows in block diagram the novel receiver of the present invention, this receiver comprises a receiver coil 26 which is adapted to be inductively coupled with the transmitting coil 23 when the transmitter oscillator is transmitting. The output of the receiver coil 26 is connected into a rectifier and filter circuit 27 which, in turn, is connected to a plurality of pulse generators 28 and 29, one for each bipolar stimulating electrode. While only two pulse generators have been shown, it is understood that an additional pulse generator can be employed for each additional bipolar electrode that may be desired. Generator 28 is in turn connected to a storage capacitor 30 and pulse generator 29 is connected to a storage capacitor 31. Storage capacitor 30 is connected to lead 11 in a manner to be presently described. Lead 12 is connected to the pulse generator 28. Similar connections are made of the electrode leads 13 and 14 to the storage capacitor 31 and the pulse generator 29.

Figure 5:
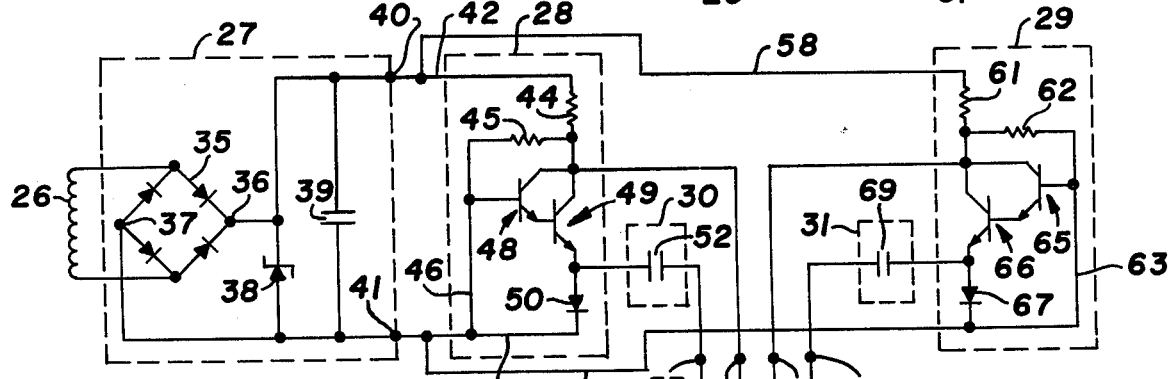
FIG. 5 is a schematic view of the implantable unit of FIG. 4 with the various components shown.

FIG. 5 shows the individual circuit components of the block diagram of FIG. 4. It will be noticed that the rectifier and filter network 27 comprises a full wave rectifier bridge 35 having its input terminals connected to the receiver coil 26 and having output terminals 36 and 37 which are connected to output terminals 40 and 41 of the rectifier and filter unit 27. A Zener diode 38 is connected across the output terminals of the rectifier bridge 35, this Zener diode having a breakdown voltage of 33 volts so that it conducts whenever the voltage across the output terminals 36 and 37 of the rectifier bridge exceeds 33 volts. The Zener diode thus acts to guard against unusually high output voltages from the rectifier bridge. Connected in parallel with the Zener diode 38 is a capacitor 39 which tends to filter out the high frequency ripple voltage so that the voltage appearing across output terminals 40 and 41 is a relatively smooth DC voltage, terminal 40 being positive with respect to terminal 41.

Referring now to the pulse generator 28, this includes two conductors 42 and 43 connected to the output terminals 40 and 41 of the rectifier and filter which act as a power supply for the pulse generator 28 and the storage capacitor 30. A first resistor 44 and a second resistor 45 are connected in series between the conductors 42 and 43 by a conductor 46. The resistor 45 is connected between the collector and base of an NPN transistor 48 which is coupled with a further NPN transistor 49 in a Darlington circuit. The voltage appearing across resistor 45 is thus applied between the collector and base of transistor 48 to prevent flow of collector emitter current from transistor 48 to the base of the other transistor 49 of the Darlington configuration and hence to prevent current flow between the collector and emitter of transistor 49. Transistor 49 is thus normally maintained non-conductive as long as a voltage is being applied to conductors 42 and 43 from the rectifier and filter network 27 constituting the power supply.

The storage capacitor unit 30 is shown as comprising a capacitor 52 which has one terminal connected to the emitter of transistor 49 and through a diode 50 to negative conductor 43. The opposite terminal of capacitor 52 is connected to a terminal 53 of the receiver unit 10 to which electrode lead 11 is connected. There is also another terminal 54 to which electrode lead 12 is connected and this terminal 54 is connected to the collectors of transistors 48 and 49 and through resistor 44 to the positive conductor 42. Thus, while a signal is being received by coil 26 resulting in an output voltage at terminals 40 and 41, a charging circuit exists from terminal 40 through conductor 42, resistor 44, terminal 54, electrode lead 12 of electrode 17, through the portion of the tissue between electrode leads 11 and 12, electrode lead 11, terminal 53, capacitor 52, diode 50 and conductor 43 to the negative power supply terminal 41. Inasmuch as transistor 49 is nonconductive due to the presence of the output voltage at terminals 40 and 41, the capacitor 52 cannot discharge through the collector emitter path of transistor 49. Furthermore, due to the diode 50, the capacitor 52 cannot discharge through any path including conductors 42 and 43.

It will be recalled that the 300 kilohertz output to the oscillator 22 is interrupted by the trigger generator 24 for 1½ milliseconds every 50 milliseconds. Whenever this happens, the receiver coil 26 no longer picks up a signal and the voltage across terminals 40 and 41 drops to zero. The capacitor 39, being merely a filter capacitor does not have sufficient capacity to maintain the voltage across terminals 40 and 41 during the 1½ millisecond interruption and discharges rapidly through the parallel combinations of resistors 44, 45 and 61, 62 and any additional impedance present at terminals 40 and 41. The voltage no longer exists between conductors 42 and 43, under these conditions and a voltage drop no longer occurs across resistor 45. The base thus tends to be at the same potential as the collector. A base emitter current can now flow. While there is no longer a voltage between conductors 42 and 43, the capacitor 52 has a voltage thereacross, the polarity of which is such that the right hand terminal thereof which is connected to the collector of transistor 49 through the electrode leads 11 and 12 and a portion of the bladder tissue, is positive with respect to the left hand terminal of the capacitor. Thus, a current flow takes place between the collector and emitter of transistor 49. The impedance of the collector-emitter circuit becomes relatively low and capacitor 52 is very quickly discharged through electrode leads 11 and 12. Capacitor 52 will continue to discharge for approximately 1½ milliseconds, the period of interruption of the output of oscillator 22. After the interruption, the oscillator 22 again provides an output which is applied to transmitter coil 23 and is inductively picked up by transmitter coil 22. Again a voltage appears across conductors 42 and 43 to cause a voltage drop across the resistor 45. This, in turn, will turn off transistor 48 to, in turn, turn off transistor 49. Furthermore, it is now possible again for capacitor 52 to be recharged due to the fact that transistor 49 is no longer conductive. Thus, as long as the transmitter is turned on by actuation of the push button 21, a voltage pulse will be applied to electrode 17 every 50 milliseconds. These periodically applied pulses are effective to stimulate the bladder to cause the bladder to discharge.

As noted above, there is a second bipolar electrode 18 formed by electrode leads 13 and 14. As indicated by the block diagram of FIG. 4, these electrode leads 13 and 14 are connected to a separate storage capacitor 31 which is controlled by a separate pulse generator 29 under the control of the same rectifier and filter as controls pulse generator 28 and storage capacitor 30. The purpose of providing two separate circuits from the power supply to energize electrode leads 11 and 12 on the one hand and 13 and 14 on the other is to insure against any current path being established from bipolar electrode 17 through the bladder tissue to bipolar electrode 18. As will be clear from the subsequent description, there is one current path between electrode leads 11 and 12 and a completely separate current path between electrode leads 13 and 14.

Referring now to the means for applying voltage pulses to electrode leads 13 an 14, it will be noted that there is also connected to output terminals 40 and 41 of the rectifier and filter unit 27 two conductors 58 and 59. Connected in series across conductors 58 and 59 are two resistors 61 and 62. Resistor 62 is connected between the collector and base of an NPN transistor 65 which is connected in a Darlington configuration with a second NPN transistor 66. Just as the voltage drop across resistor 45 maintained transistor 48 nonconductive so does the voltage drop across resistor 62 maintain the transistor 65 and hence transistor 66 nonconductive. The capacitor unit of storage capacitor 31 is indicated by the reference numeral 69. This is connected to a power supply and to transistor 66 in the same manner as is capacitor 52 connected to transistor 49 and to the power supply. Again, a rectifier 67 is connected between the emitter of transistor 66 and the negative conductor 59. The collector of transistor 66 is connected to a terminal 72 which is connected to the electrode lead 13. The left hand terminal of capacitor 69 is connected to a terminal 73 which in turn is connected to electrode lead 14.

The operation of the pulse generator 29 and the capacitor 31 should be readily apparent in view of the foregoing description of the similar units 28 and 30. In other words, as long as the voltage appears at terminals 40 and 41, a positive voltage is applied to conductor 58 and a relatively negative voltage to conductor 59. This will maintain transistors 65 and 66 nonconductive in the manner described. Furthermore, the capacitor 69 will be charged by a circuit extending from conductor 58 through resistor 61, a conductor extending to terminal 72, electrode lead 13, through a portion of the bladder, electrode lead 14, terminal 72, capacitor 69 and diode 67 to the relatively negative conductor 59. Each time that the output of oscillator 22 is interrupted, transistors 65 and 66 will become conductive and capacitor 69 will discharge through the electrode leads 13 and 14 and the collector-emitter path of transistor 66. Thus, each time that the voltage pulse is applied to electrode leads 12 and 31, a voltage pulse is applied to electrode leads 13 and 14. While the voltage pulses are applied simultaneously to electrode leads 12 an 13 on the one hand and electrode leads 14 and 15 on the other hand, it will be noted that there is no direct conductive path between the two sets of electrodes.

While we have shown only two bipolar electrodes 17 and 18, it will be understood that other such electrodes can be employed by connecting further pulse generators to terminals 40 and 41 in the same manner as pulse generator 29 is connected. In such an arrangement, each such pulse generator would be connected to a separate storage capacitor and a separate set of electrode leads.

While the invention is not limited to the use of components having any specific values, components having the following values were employed in one unit. In such unit, the transmitter frequencies were those named above.

Resistors
44, 61 — 470 ohm
45, 62 — 6.8 kilohms
Capacitors
39 — 0.1 microfarad
52, 69 — 22 microfarads
Diodes
Forward current — 400 milliamps. max.
Reverse voltage — 85 volts min.

MODIFICATION OF FIGURE 6

Figure 6:
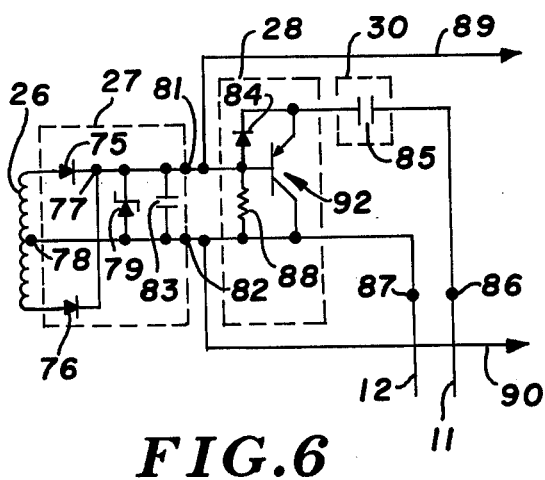
FIG. 6 is a schematic view showing a modified form of the implantable unit.
Figure 7:
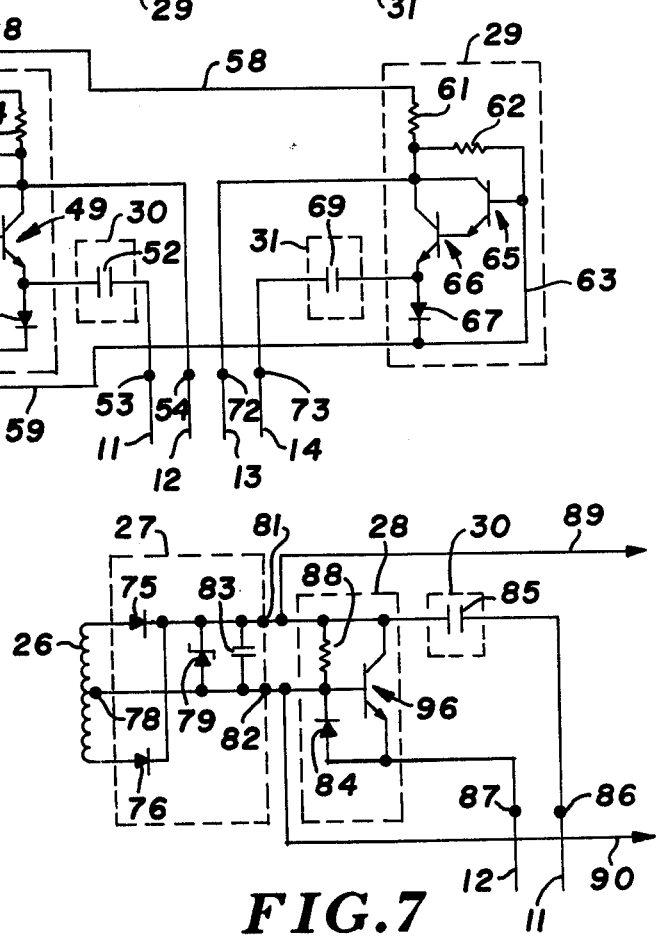
FIG. 7 is a further modification, in schematic form, of the implantable unit.

The embodiments described in FIG. 6 and FIG. 7 are included here to more fully describe the invention by illustrating how different circuit configurations and appropriate polarity changes can be used to accomplish the same self-discharging pulse generating features of the invention.

While the arrangement of FIG. 6 is basically similar in operation to FIG. 5, there are certain differences. For one thing, the rectifier and filter unit are somewhat different and the transistors employed are PNP transistors which, of necessity, result in certain differences.

Referring first to the rectifier and filter circuit, this circuit, instead of employing a bridge type full wave rectifier circuit, employs a type of circuit in which there is a center tap 78 on the receiver coil 26. There are two rectifier diodes 75 and 76. This is a well known type of full wave rectifier circuit and in such a rectifier circuit, there is an output terminal 77 at which a positive voltage appears and an output terminal constituted by the center tap 78 at which a relatively negative voltage appears. A Zener diode 79 is connected across the terminals 77 and 78 to protect against any excessive voltages appearing. Normally, the Zener diode 79 is non-conductive. A capacitor 83 is also connected across the terminals 77 and 78 to tend to filter out the high frequency ripple voltage that is present at the output terminals. The filtered and rectified voltage is applied to output terminals 81 and 82. A resistor 88 is connected across the output terminals 81 and 82 so that the full output voltage appears across resistor 88. Resistor 88 is, in turn, connected between the base and collector of a PNP transistor 92. A rectifier 84 is connected between the emitter of transistor 83 and the base.

When there is a voltage being transmitted by the oscillator 22 of the transmitting unit so that a voltage appears across output terminals 81 and 82 of the rectifier and filter unit, the base is maintained relatively positive with respect to the collector and the base emitter voltage is maintained positive to the extent of the forward conduction voltage of rectifier 84. The result of this is that transistor 92 is held non-conductive and no emitter base current and hence no emitter collector current will flow as long as a signal is being transmitted by the transmitter.

In this modification of FIG. 6, the storage capacitor 30 comprises a capacitor 85 which has one terminal connected to the positive terminal 81 of the power supply through the rectifier 84. The opposite terminal of capacitor 85 is connected to terminal 86 which in turn is connected to electrode lead 11. It will be appreciated that the other electrode lead 12 is connected to terminal 87 which in turn is connected to the negative terminal 82. Thus, when a voltage appears across terminals 81 and 82, a charging circuit for the capacitor 85 occurs from the positive terminal 81 through diode 84, capacitor 85, and the electrode leads 11 and 12 back to the more negative terminal 82. Thus, the capacitor 85 will assume a charge such that the left hand terminal is positive with respect to the right hand terminal. This charge remains until the transistor 92 becomes conductive, as will be explained presently.

Just as in the preferred embodiment of FIG. 5, the transistor 92 is held non-conductive as long as the voltage is being received by the receiving coil 26. As soon as this ceases, however, the voltage across resistor 88 ceases to exist with the result that the potential of the base of transistor 92 now becomes the same as that of the collector so that current flow can take place between the emitter and the base, causing the emitter, collector path to become conductive. A circuit is now established from the left hand or positive terminal of capacitor 85 through the emitter, collector path of transistor 92 through terminal 87 to electrode lead 12, through the portion of the bladder, through the other electrode lead 11 to terminal 86, and back to the right hand terminal of capacitor 85. The result is that the capacitor 85 will be rapidly discharged and will apply a voltage pulse to electrode leads 11 and 12 to stimulate the bladder.

Also connected to output terminals 81 and 82 of the rectifier and filter network 27 are two conductors 89 and 90 which will extend to another pulse generator and storage capacitor associated with another pair of electrode leads.

It will be appreciated that the unit of FIG. 6 basically operates in exactly the same manner as that of FIG. 5. In each case, the electronic current control device, taking the form of a transistor, allows the storage capacitor to apply a charge to electrodes whenever the transmitted voltage ceases to exist. There is no necissity of a separate trigger voltage being applied to a transistor or SCR. The transistor simply becomes conductive as soon as the received voltage disappears. Thus, as with FIG. 5, the arrangement results in an extremely simple circuit.

MODIFICATION OF FIG. 7

The arrangement of FIG. 7 is similar to that of FIG. 6 in the type of rectifier and filter employed. In this case, however, an NPN transistor is employed and a somewhat different arrangement is used for controlling this transistor.

Referring specifically to the drawing, the same reference characters are used in the various elements of the rectifier and filter network as are used in connection with FIG. 6 and it is believed unnecessary to repeat the description. As in FIG. 6, there are two output terminals 81 and 82 across which a voltage appears whenever a signal is detected by the receiver coil 26. In the present case, as in FIG. 7, the resistor 88 is connected between the terminals 81 and 82 and between the collector and base of the transistor 96 which, as previously noted is an NPN transistor. The primary difference is that the positive terminal of resistor 88 is connected to the collector and the more negative terminal to the base. In FIG. 6, it was the positive terminal that was connected to the base and the more negative to the collector. The reason for this difference is that the transistor 96 in the modification of FIG. 7 is an NPN transistor whereas the transistor 92 in FIG. 6 is a PNP transistor.

As in FIG. 6, a rectifier 84 is connected between the base and emitter. This rectifier, as in all of the modifications, is in the charging circuit for the capacitor 85 which is the capacitor unit of the storage capacitor 30.

It is believed that the operation will be fairly obvious. Whenever a positive voltage appears at terminal 81, a voltage drop will appear across resistor 88 which will tend to hold the base of transistor 96 at a voltage highly negative with respect to the emitter. The result will be that there will be a relatively small voltage drop between the base and emitter so that no current flow will take place through the collector emitter path. During this time, the capacitor 85 will charge through a path from terminal 81, including capacitor 85, electrode lead 11, through the bladder tissue, the electrode lead 12, and rectifier 84 back to the more negative terminal 82. Each time that the transmitter ceases to send a voltage, the voltage across terminals 81 and 82 disappears with the result that the potential of the base tends to rise with respect to the emitter so as to cause current flow through transistor 92. This will provide a discharge path for capacitor 85 through the emitter collector path of transistor 92 and through the electrode leads 12 and 13. As with all of the other modifications, this occurs each time that the trigger generator 24 of the transmitter interrupts the output of the oscillator.

SUMMARY

It will be noted that in each of the three modifications, the storage capacitor is discharged by reason of the received voltage being temporarily terminated. It is thus not necessary to provide any special triggering means for triggering a transistor or SCR. The mere disappearance of the input voltage results in a change in the comparative values of the base and emitter voltages so as to cause conduction of the transistor to cause discharge of the associated capacitor. Furthermore, even though the power supply for the transistors has momentarily disappeared due to the interruption of the transmitter oscillator output, the transistor still becomes conductive by reason of the charged capacitor connected thereto.

The result is an extremely simple circuit with a minimum of parts. This is very important in connection with an implantable unit. In the first place, it is desirable to keep the overall size of the implantable unit as small as possible. In the second place, while the components involved are extremely reliable and have very long life, it is still obvious that the fewer components there are, the less will be the danger of a failure due to some very abnormal situation. The arrangement of the present invention provides for the absolute minimum in the number of components, all of which components are extremely stable items very unlikely to fail in operation.

While we have shown certain specific embodiments of our invention for purposes of illustration, it is to be understood that the scope of the invention is limited solely by that of the appended claims.

We claim:

1. Apparatus for periodically stimulating an internal body organ under the selective control of a device located outside of the body, said apparatus comprising:
   an external transmitter unit having means for producing a relatively high frequency output and means for periodically effectively interrupting said high frequency output: and
   an implantable unit including
      a power supply portion having output terminals and means reactively coupled with said transmitter unit when the latter is in proximity to said implantable unit for producing a D.C. voltage across said output terminals during each duration of the high frequency output,
      at least one electrode adapted to be affixed adjacent the organ to be stimulated,
      an energy storage device,
      an electronic switching device having control elements which cause said electronic switching device to be non-conductive when a voltage of at least a predetermined value is applied between said elements,
      circuit means connecting said energy storage device, said electrode, and said electronic switching device in series,
      means connecting said power supply portion to said energy storage device to cause energy to be stored in the latter while said switching device is in non-conducting condition,
      and means connected across the output terminals of said power supply portion and to said control elements of said switching device for deriving from said power supply portion and applying to said control elements a voltage of at least said predetermined value so that said switching device is non-conductive while said power supply portion is supplying a voltage and means for causing said switching device to become conductive each time said voltage ceases, to cause said energy storage device to cause periodic energization of said electrode to stimulate said organ.

2. The apparatus of claim 1 in which the external transmitter has a transmitting coil to which said high frequency output is applied and in which said means reactively coupled with said transmitter unit includes an inductive coil inductively coupled with said transmitter coil when said transmitter unit is in proximity to said implantable unit.

3. The apparatus of claim 1 in which said energy storage device is a capacitor which is charged while said electronic switching device is non-conductive.

4. The apparatus of claim 1 in which said means for deriving a voltage includes impedance means and in which said electronic switching device is a transistor having a collector and emitter in series with said energy storage device and said electrode, and means including a connection of the base to said impedance means for preventing any substantial current flow taking place in the emitter-collector circuit during the existence of said voltage produced by said power supply portion.

5. The apparatus of claim 4 in which said impedance means is a resistor connected across the output terminals of said power supply portion and between the base and collector of said transistor.

6. The apparatus of claim 5 in which there is a second resistor connected in series with said resistor between the collector and the positive output terminal of said power supply portion.

7. The apparatus of claim 4 in which the voltage drop across said impedance means is the only biasing voltage for maintaining said electronic switching device non-conductive while said power supply portion is supplying a voltage.

8. The apparatus of claim 1 in which said power supply unit comprises a rectifier for rectifying the high frequency voltage and a constant voltage device connected across the output to limit the voltage to a predetermined value.

9. The apparatus of claim 1 in which the only source of energy in said implantable unit is the energy derived by said power supply portion by reason of the reactive coupling with said transmitter unit so that each time said voltage ceases, the source of energy for said electronic switching device is that obtained from said energy storage device.

10. The apparatus of claim 1 in which there are two electrodes adapted to be fixed adjacent the organ to be stimulated and in which there is a separate energizing means for energizing each electrode, each energizing means comprising an energy storage device, an electronic switching device, a circuit means for connecting the energy storage device, the electrode, and the switching means in series, means for connecting said power supply means to the energy storage means, and means for causing said energy storage device to cause periodic energization of the associated electrode, all as set out in claim 1, said energizing means for said two electrodes being both connected in parallel to said power supply portion.

* * * * *